United States Patent
Freundlich

(12) 
(10) Patent No.: US 6,522,142 B1
(45) Date of Patent: Feb. 18, 2003

(54) MRI-GUIDED TEMPERATURE MAPPING OF TISSUE UNDERGOING THERMAL TREATMENT

(75) Inventor: David Freundlich, Haifa (IL)

(73) Assignee: InSightec-TxSonics Ltd., Tirat Carmel (IL)

(*) Notice: Subject to any disclaimer, the term of this patent is extended or adjusted under 35 U.S.C. 154(b) by 0 days.

(21) Appl. No.: 10/022,758

(22) Filed: Dec. 14, 2001

(51) Int. Cl.[7] ............................................. A61B 5/055
(52) U.S. Cl. ........................ 324/315; 324/318; 324/309
(58) Field of Search .............................. 324/315, 318, 324/309, 322, 307; 600/411, 421

(56) References Cited

U.S. PATENT DOCUMENTS 5,378,987 A * 1/1995 Ishihara et al. .............. 324/315
6,128,522 A * 10/2000 Acker et al. ................. 600/411
6,374,132 B1 * 4/2002 Acker et al. ................. 600/411

FOREIGN PATENT DOCUMENTS

EP          0 560 397    *  3/1993  .......... G01R/33/52

* cited by examiner

Primary Examiner—Edward Lefkowitz
Assistant Examiner—Brij B. Shrivastav
(74) Attorney, Agent, or Firm—Bingham McCutchen LLP

(57) ABSTRACT

Systems and methods using magnetic resonance imaging for monitoring the temperature of a tissue mass being heated by energy converging in a focal zone that is generally elongate and symmetrical about a focal axis. A first plurality of images of the tissue mass are acquired in a first image plane aligned substantially perpendicular to the focal axis. A cross-section of the focal zone in the first image plane is then defined from the first plurality of images. A second plurality of images are acquired of the tissue mass in a second image plane aligned substantially parallel to the focal axis, the second image plane bisecting the first image plane at approximately a midpoint of the defined focal zone cross-section.

22 Claims, 3 Drawing Sheets

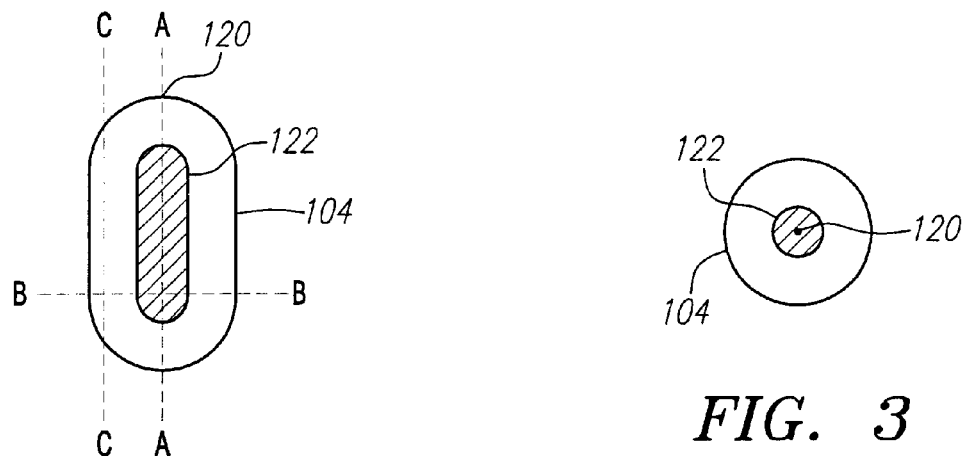
FIG. 2
FIG. 3
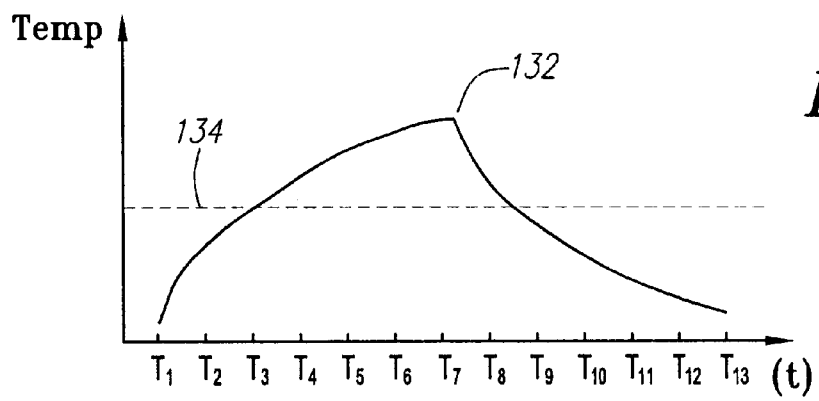
FIG. 4
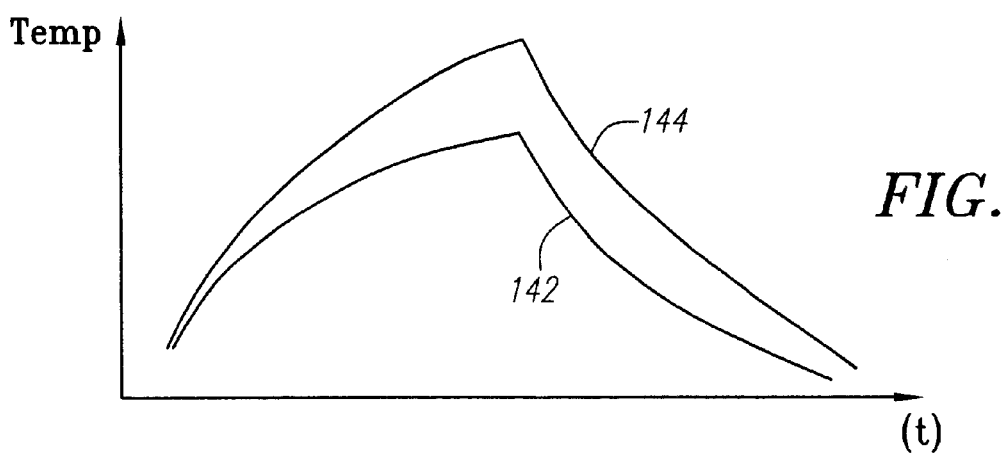
FIG. 5

MRI-GUIDED TEMPERATURE MAPPING OF TISSUE UNDERGOING THERMAL TREATMENT

BACKGROUND

1. Field of the Invention

The present invention relates generally to magnetic resonance imaging (MRI) guided thermal treatment systems, and more particularly to using MRI to obtain thermal evolution images of a tissue mass undergoing thermal treatment.

2. Background of the Invention

Certain types of body tissues, such as tumors, can be destroyed by heat. One way to apply thermal energy to internal body tissue is to focus high intensity, ultrasonic acoustic waves into the tissue using, e.g., a phased-array of piezoelectric transducers. Such treatment can reduce or even eliminate the need for invasive surgery to remove the tissue. Of critical importance to the treatment process is verifying that a sufficient thermal dose is reached during each application of ultrasonic energy (or "sonication") to kill/ablate the portion of the target tissue structure being heated. It is also important to be able to precisely track which portions of the tissue structure have been killed/ablated, in order to minimize the total number of sonications needed in a particular treatment session.

Towards this end, MRI systems are used to assist in aiming ultrasonic wave energy at a target tissue structure in a body, and to monitor the temperature change of the tissue region being heated during the thermal treatment process to ensure that a sufficient thermal dose is reached to fully ablate the tissue being heated.

One method of measuring temperature change using MRI techniques exploits the temperature dependence of the proton resonant frequency (PRF) in water. The temperature dependence of the PRF is primarily due to temperature-induced rupture, stretching, or bending of the hydrogen bonds in water. The temperature dependence of pure water is 0.0107 ppm/° C., and the temperature dependence of other water-based tissues is close to this value. Because of a non-homogenous magnetic field within the MRI machine, absolute PRF measurements are not possible. Instead, changes in PRF are measured by first taking a MR image before the delivery of heat, and subtracting this baseline value from subsequent measurements. The temperature-induced changes in PRF are then estimated by measuring changes in phase of the MR signal, or frequency shift, in certain MR imaging sequences.

Notably, the duration of each sonication must be limited, e.g., to approximately ten seconds, in order to avoid the unwanted (and painful) build up of heat in healthy tissue surrounding the target tissue structure being heated. Thus, there is limited time for acquiring temporal MR images for monitoring the temperature increase during a sonication in order to verify a sufficient kill temperature has been reached. Because it can take at least one and as much as much as three seconds to acquire a single MR thermal sensitive image, this means there is little room for-using a multi slice MR imaging techniques to cover the whole heated volume.

SUMMARY OF THE INVENTION

The invention is directed to systems and methods using magnetic resonance imaging for monitoring the temperature of a tissue mass undergoing thermal treatment by energy converging in a generally elongate focal zone symmetrical about a focal axis.

In one embodiment, a system is configured to acquire a first plurality of images of the tissue mass in a first image plane aligned substantially perpendicular to the focal axis. A cross-section of the focal zone in the first image plane is defined from the first plurality of images. A second plurality of images of the tissue mass are also acquired in a second image plane aligned substantially parallel to the focal axis, the second image plane bisecting the first image plane at approximately a midpoint of the defined focal zone cross-section.

In one embodiment, the first plurality of images includes a baseline image taken prior to the application of ultrasound energy to the tissue mass.

In one embodiment, one image of the second plurality of images is acquired proximate the end of an ultrasound sonication.

In one embodiment, the system is configured to further acquire one or more additional images of the tissue mass in the focal zone in a third image plane aligned substantially perpendicular to the focal axis while acquiring the images of the second plurality of images. A cross-section of the focal zone in the third image plane is then defined from the additional images, whereby it may be verified that the second imaging plane bisects the third image plane at approximately a midpoint of the defined focal zone cross-section in the third image plane.

In preferred embodiments, the system is further configured to derive a three-dimensional thermal evolution of the tissue mass in the focal zone based on the first and second pluralities of images. In one embodiment, the thermal evolution is derived by defining a cross-section of the focal zone in the second image plane from the second plurality of images, the cross-section of the focal zone in the second image plane having a length. The cross-section of the focal zone in the first image plane is extrapolated along the length of the cross-section of the focal zone in the second image plane. The thermal evolution is then generated based on differences in a characteristic of the tissue mass in the focal zone measured in successive images of the second plurality of images, wherein the differences correspond at least in part to changes in temperature of the tissue mass between respective images.

In one embodiment, the measured characteristic is a phase of an electromagnetic signal emitted from the tissue mass, and wherein the corresponding temperature change is derived from a phase shift in the signal between successive images.

In one embodiment, the thermal evolution is used to verify that the temperature of the tissue mass in the focal zone exceeded a threshold temperature.

Other aspects and features of the invention will become apparent in view of the disclosed and described embodiments.

BRIEF DESCRIPTION OF THE DRAWINGS

Preferred embodiments and implementations of the invention are now shown and described in conjunction with the following drawings, in which:

FIG. 2 is a cross-sectional view of the focal zone taken in a first imaging plane parallel to a focal axis of the ultrasound beam;

FIG. 3 is a cross-sectional view of the focal zone taken in a second imaging plane perpendicular to the focal axis of the ultrasound beam;

FIG. 4 is a graph illustrating the temporal temperature change of the tissue the focal zone taken in a given image plane;

FIG. 5 is a diagram illustrating differences in the temperature change detected by MR imaging of the focal zone, depending on where the MR imaging plane is aligned.

DETAILED DESCRIPTION OF PREFERRED EMBODIMENTS OF THE INVENTION

Figure 1:
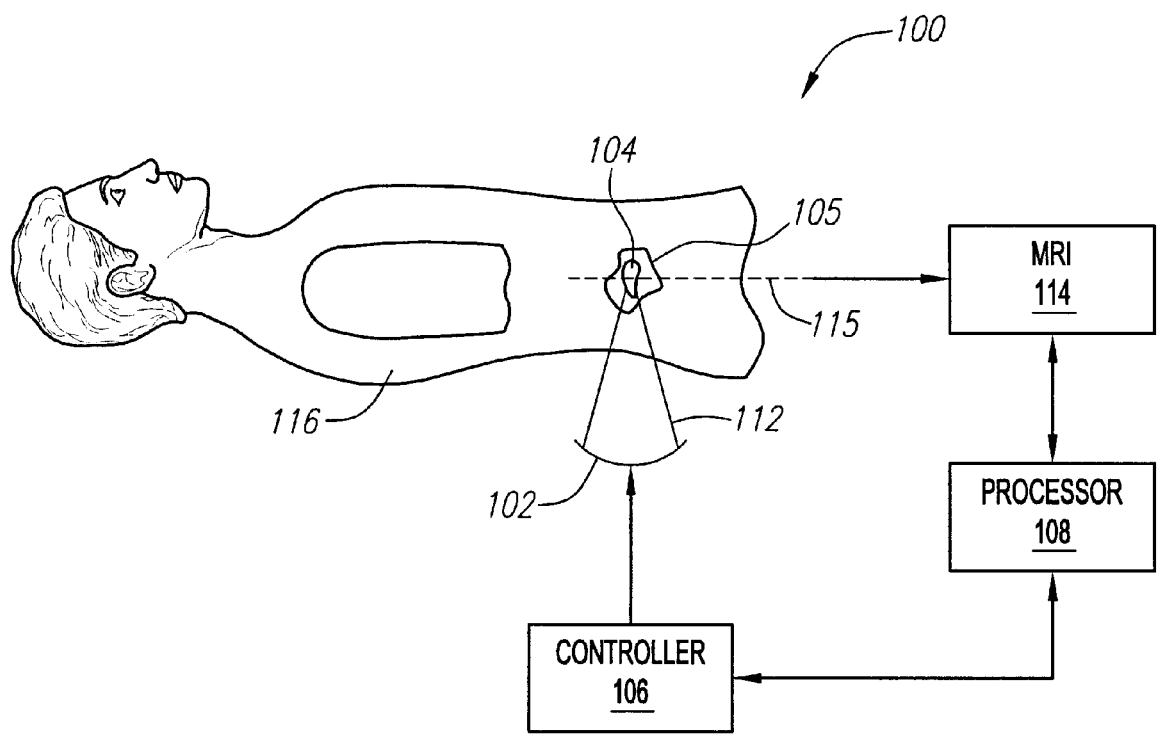
FIG. 1 is a simplified schematic illustration of a MRI-guided focussed ultrasound thermal treatment system emitting a converging ultrasound beam to a focal zone in a target tissue mass located in a patient.

FIG. 1 is a simplified schematic illustration of an exemplary MRI-guided focussed ultrasound thermal treatment system 100. The system 100 includes a phased array transducer 102 driven by a controller 106 for emitting a beam of focussed ultrasound energy 112 converging in a focal zone 104 located in a target tissue mass 105 in a patient 116. The geometry of the focal zone 104 within the target tissue structure 105 is a function of the shape of the transducer 102 and phasing of the individual transducer elements, which dictate the interaction of the converging ultrasonic waves. In the illustrated embodiment, the transducer is a concave, spherical cap, such the focal zone 104 will have a generally elongate shape, symmetrical about a focal axis, as shown in FIGS. 2 and 3.

Thermal conduction in the tissue mass 105 and cooling blood flow may also play a role in the actual thermal energy distribution in the tissue mass 105. Also, for a given output power of the energy beam 112 and volume of the focal zone 104, a longer sonication results in higher tissue temperature within the focal zone 104, and greater heat transfer through conduction to tissue adjacent the focal zone 104. Importantly, to avoid near field heating of non-target tissue, as well as secondary hot spots, there are practical limits to both the duration of the sonication and the energy level of the ultrasound beam 112. Thus, the actual tissue volume being heated may vary somewhat from the initial boundaries of the ultrasound beam focal zone 104. For purposes of simplification in describing the invention herein, it is presumed herein that the boundary of the focal zone 104 is defined as the tissue volume that receives significant thermal energy, whether directly from the ultrasound energy, or indirectly from thermal conduction.

A MRI system 114 is used to acquire images taken along a two-dimensional image plane (or slice) 115 passing through a portion of the focal zone 104. The acquired images are processed by a processor 108 to monitor the change in temperature of this portion of the tissue mass 105. The tissue temperature changes measured from images acquired in one or more imaging planes 115 are used to derive a three-dimensional thermal evolution of the entire focal zone 104. The thermal evolution is used to verify that a sufficient tissue "kill" thermal dose is reached in the focal zone 104, as well as to track which portions of the tissue 105 have been killed. This information, in turn, is used by the ultrasound controller 106 for positioning the ultrasound energy beam 112 and focal zone 104 for successive sonications of the tissue mass 105. Thus, it is critical that the thermal evolution of the three-dimensional focal zone 104 be accurate.

More particular aspects, features, embodiments, and preferred systems and methods for operating an MRI-guided focussed ultrasound system, such as system 100, are disclosed in commonly owned U.S. patent application Ser. Nos. 09/556,095, 09/557,078, 09/724,611, 09/724,670, 09/871, 464, and 09/884,206, which are each incorporated by reference herein.

FIGS. 2 and 3 depict cross-sectional images of the focal zone 104 taken in orthogonal imaging planes. Notably, the focal zone 104 is substantially elongate in shape and symmetrical along a focal axis 120 of the ultrasound transducer 102. The cross-sectional view of the focal zone 104 shown in FIG. 2 is taken in an image plane parallel to, and in this instance including the focal axis 120, referred to herein as a "vertical" image plane. The cross-sectional view of the focal zone 104 shown in FIG. 3 is taken in an image plane perpendicular to the focal axis 120, (along line B—B in FIG. 2), referred to herein as a "horizontal" image plane. Notably, images taken in a horizontal image plane are easier to locate such that they will intersect the heated zone along the focal axis 120, whereas images taken in a vertical image plane may or may not intersect the heated zone along the focal axis 120.

FIG. 4 is a graph of the temperature change of the tissue in the focal zone taken in a selected image plane over the course of a sonication. In particular, the graph depicts changes in tissue temperature (at one pixel) in the image plane corresponding to differences in a characteristic of the tissue measured in successive MR images $T_1$–$T_{13}$ taken in the particular image plane. In one embodiment, the measured characteristic is a phase of an electromagnetic signal emitted from the tissue, wherein the corresponding temperature change is estimated based on a phase shift in the signal between successive images.

At time $T_1$, which is preferably just before initiation of the sonication, the MRI system 114 acquires a first image, which is used to establish a baseline of the measured tissue characteristic, presumably reflecting body temperature of the patient 116. The application of ultrasonic energy then commences and a second image is acquired at time $T_2$. From this second image, the thermal evolution, i.e., change in tissue temperature, from time $T_1$ to $T_2$ in the respective image plane can be estimated from the change in the measured tissue characteristic. Successive temporal images are taken as the tissue is being heated. The actual number of images that can be acquired while the tissue is being heated may vary between embodiments and depend, e.g., on the imaging modality of the MRI system.

The process of acquiring images in the respective image plane continues at least to the end of the sonication period, i.e., until the application of ultrasonic energy ceases. In the graph of FIG. 4, the application of ultrasonic energy continues to time $T_7$, at which point accumulated heat in tissue reaches a peak temperature 132. The processor 108 uses the images acquired at times $T_1$–$T_{13}$ to ensure that the heat transferred to the tissue 105 in the focal zone 104 exceeds a predetermined "kill threshold" thermal dose.

In order to derive an accurate three-dimensional temperature evolution of the focal zone 104, it would seem necessary to be able to track the temperature map changes in both horizontal and vertical image planes, including a sufficient number of planes covering the entire focal zone. However, this is not possible, since the acquired images are taken along thin "slices" of the tissue and require a relatively long time to acquire with respect to the limited sonication time. This is particularly problematic with images taken in a vertical image plane of the focal zone 104. As seen in FIGS. 2 and 3, the thermal energy is most concentrated, and thus a higher temperature is reached, in an elongate-shaped center 122 of the focal zone 104. Thus, it is readily apparent that images acquired in a vertical imaging plane taken along line C—C in FIG. 2 will not accurately depict the true thermal evolution map of the focal zone. In particular, unless images acquired in a vertical image plane either include the focal axis 120, a true thermal evolution map will not be obtained.

To better illustrate the foregoing points, FIG. 5 shows the thermal evolution 142 (temperature change v. time) of a point in an image slice taken along vertical image plane C—C of FIG. 2, versus the thermal evolution 144 of a point in an image slice taken in a vertical image plane taken along line A—A including the focal axis 120. Thus, in order for processor 108 to generate a more accurate estimate of the thermal evolution of the focal zone 104, the thermal images acquired by the MRI system 114 during the sonication should be taken in a vertical plane located as close to the focal axis 120 as possible. If the images are taken in a vertical plane to too distant from the focal axis 120, the processor 108 will under estimate the thermal evolution of focal zone 104, as would be the case with the thermal evolution 142 illustrated in FIG. 5. As noted above, because the temporal period of successive image acquisitions is between 1 to 3 seconds, and the application of ultrasonic energy in a given sonication is for a relatively short period, e.g., 10 seconds, there is not adequate opportunity to adjust the alignment of the vertical imaging plane during as sonication.

In accordance with the present invention, the processor 108 is configured to acquire a plurality of images of the tissue mass 105 in a horizontal image plane (i.e., aligned substantially perpendicular to the focal axis), which is relatively easy to locate somewhere along the focal zone given the generally elongate shape of the focal zone 104.

In one embodiment, the plurality of horizontal images include a baseline image taken just prior to the sonication, and a further image taken after the heating has commenced, such that a temperature change will appear between the two images. From the temperature change, the boundary of a cross-section of the focal zone 104 in the horizontal image plane can be determined by the processor 108. At the same time the plurality of horizontal images are being acquired, a plurality of images in a vertical imaging plane are also acquired, i.e., in an interleaved mode, wherein the vertical imaging plane is established to be at the midpoint of the defined focal zone cross-section. Because the focal zone 104 is generally symmetrical about the focal axis 120, the midpoint of the defined cross-section will be approximately aligned with the focal axis 120, such that the vertical plane will either encompass the focal axis 120, or otherwise be sufficiently close to the focal axis to provide an accurate reflection of the thermal evolution of the focal zone 104. In particular, the acquired horizontal thermal images will show whether the vertical thermal images are actually close enough to the midline of the focal zone. If not, the operator is able to adjust the vertical imaging plane so that, at the next application of energy, the vertical imaging plane will be at the midpoint of the focal zone.

Figure 6:
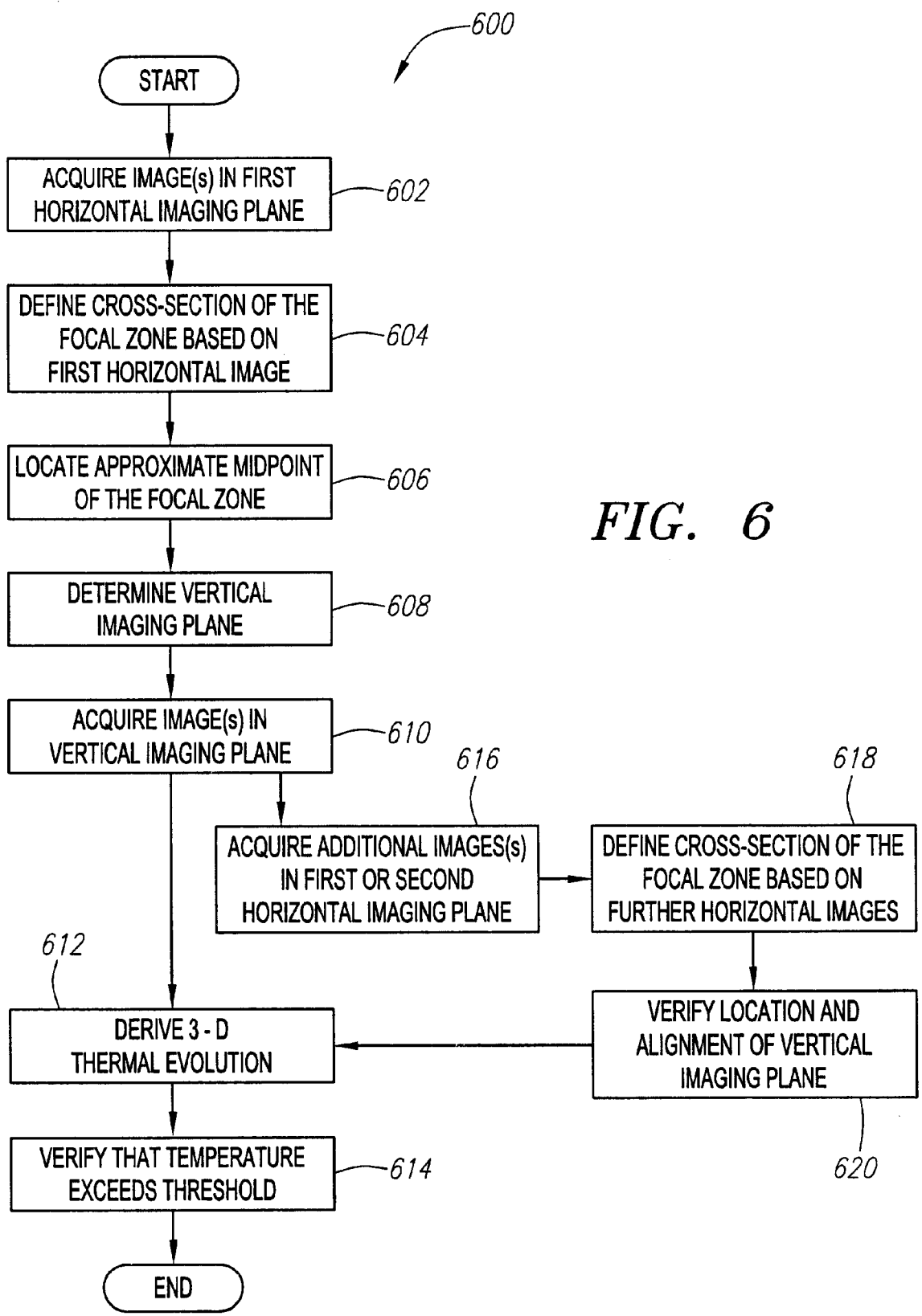
FIG. 6 is a flow chart illustrating an exemplary process by which the thermal evolution of the target tissue structure can be monitored, ensuring proper alignment of the MR imaging plane with the focal zone.

One embodiment of the invention is a method 600 for acquiring images sufficient to generate an accurate thermal evolution of tissue in a focal zone being heated by focussed energy is illustrated in FIG. 6. The method may be implemented by a software or firmware controlled processor for controlling the acquisition of MR images, and analyzing the acquired images, e.g., processor 108 in system 100. Another embodiment of the invention is a system configured to perform the method 600.

First, in step 602, a plurality of temperature images are acquired in a horizontal imaging plane, a first temperature image of the plurality preferably being a baseline image acquired prior to initiation of the sonication. In one embodiment, the horizontal temperature images include only two images in order to minimize the time and system resources needed for their acquisition.

In step 604, the focal axis of symmetry in the vertical plane is located using the temperature change measurements derived from the horizontal temperature images. Step 604 includes determining the boundaries (edges) of the focal zone lying in the first horizontal imaging plane.

In step 606, once the boundary of the focal zone is located in the horizontal imaging plane, an approximate center point of the focal zone in the respective plane is located. Because the focal zone is generally symmetrical about a longitudinal (vertical) axis of symmetry, the center point determined in this manner will also lie on the axis of symmetry for any horizontal imaging plane intersecting the focal zone.

In step 608, a vertical imaging plane is determined based on the location of center point (or "midpoint") of the focal zone in the horizontal imaging plane. In particular, the vertical imaging plane is selected to be orthogonal to the horizontal imaging plane and containing the midpoint. In step 610, which is undertaken contemporaneous with step 602, i.e., in an interleaved mode, a plurality of temperature images are acquired in the vertical imaging plane. In a preferred embodiment, the vertical temperature images are continually acquired until the heating period is ended.

In step 612, a three-dimensional thermal evolution of the portion of the tissue mass in the focal zone is derived based on the horizontal and vertical temperature images. In a preferred embodiment, the thermal evolution is derived by first defining a cross-section of the focal zone in the vertical image plane from the vertical temperature images. Because of the elongate geometry of the focal zone, the cross-section of the focal zone in the vertical image plane will have a length substantially axially aligned with the focal axis of symmetry. The cross-section of the focal zone in the horizontal plane is then extrapolated along the length of the cross-section of the focal zone in the vertical plane to arrive at an estimated focal zone geometry. By determining differences in a characteristic of the tissue mass measured in successive images of the vertical temperature images, changes in temperature of the tissue mass between respective images can also be determined.

The thermal evolution of the three-dimensional focal zone geometry is estimated based on extrapolating the temperature changes in the vertical plane across the horizontal focal zone cross section. In one embodiment, the measured tissue characteristic is a phase of an electromagnetic signal emitted from the tissue mass, wherein the corresponding temperature change is derived from a phase shift in the signal between successive images.

In step 614, the derived thermal evolution is then used to verify that the thermal dose at the tissue mass in the focal zone exceeded a threshold tissue kill thermal dose. The first and second plurality of images acquired in steps 602 and 610 can also be used to verify that the ultrasonic energy was applied at the correct location within target mass 104.

In some embodiments, it may be preferable to acquire subsequent images taken in the same or differing horizontal imaging plane(s) in order to verify that the geometry of the cross-section of the focal zone remains uniform, both with respect to any changes in the boundary during the sonication, and with respect to the uniformity of the focal zone boundaries along the entire length of the vertical image plane. Towards this end, in step 616, the system acquires one or more additional images of the tissue mass in the focal zone in a second horizontal image plane (i.e., orthogonal to the vertical imaging plane), between acquiring temporal images of the second plurality of images in the vertical plane. A cross-section of the focal zone in the second horizontal imaging plane is then defined in step 618. In step 620, it is then verified that the vertical imaging plane bisects the second horizontal imaging plane at approximately a midpoint of the defined focal zone cross-section in the second horizontal imaging plane.

The actual pattern and ratio of images acquired in the vertical imaging plane to images acquired in one or more horizontal imaging planes can vary widely depending on the embodiment. Although, preferably the ratio always includes more images in the vertical plane than in the horizontal plane(s) so that there is sufficient images taken along the longitudinal axis of the focal zone to generate an accurate estimate of the thermal evolution. The system processor may be programmed to acquire, e.g., one image in a horizontal imaging plane for every image acquired in the vertical imaging plane after the sonication has commenced. This can be especially useful if the shape of focal zone is slightly irregular.

While embodiments and implementations of the invention have been shown and described, it should be apparent that many more embodiments and implementations are within the scope of the invention. For example, while the described embodiments are directed to MR imaging of an elongate focal zone of converging ultrasound energy symmetrical about a focal axis, the same inventive concepts may also apply to temperature monitoring of a different heating modality, e.g., converging focussed light waves, or converging radio frequency electromagnetic energy.

Accordingly, the invention is not to be restricted, except in light of the claims and their equivalents.

What is claimed:

1. A method using magnetic resonance imaging for monitoring the temperature of a tissue mass being heated in a focal zone encompassing at least a portion of the tissue mass, the focal zone being generally elongate and symmetrical about a focal axis, the method comprising:

acquiring a first plurality of images of the tissue mass in a first image plane aligned substantially perpendicular to the focal axis;

defining a cross-section of the focal zone in the first image plane from the first plurality of images; and acquiring a second plurality of images of the tissue mass in a second image plane aligned substantially parallel to the focal axis, the second image plane bisecting the first image plane at approximately a midpoint of the defined focal zone cross-section, such that images acquired in the first plane are substantially orthogonal to images acquired in the second plane.

2. The method of claim 1, wherein heating energy is applied for a defined heating period, and wherein an image of the second plurality of images is acquired proximate the end of the heating period.

3. The method of claim 1, further comprising deriving a three-dimensional thermal evolution of the portion of the tissue mass in the focal zone based on the first and second pluralities of images.

4. The method of claim 3, wherein the thermal evolution is derived by defining a cross-section of the focal zone in the second image plane from the second plurality of images, the cross-section of the focal zone in the second image plane having a length, and extrapolating the cross-section of the focal zone in the first image plane along the length of the cross-section of the focal zone in the second image plane.

5. The method of claim 3, further comprising verifying that the temperature of the tissue mass in the focal zone exceeded a threshold temperature or thermal dose based on the derived thermal evolution.

6. The method of claim 1, further comprising acquiring one or more additional images of the tissue mass in the focal zone in a third image plane aligned substantially perpendicular to the focal axis while acquiring the images of the second plurality of images, defining a cross-section of the focal zone in the third image plane, and verifying that the second imaging plane bisects the third image plane at approximately a midpoint of the defined focal zone cross-section in the third image plane.

7. A method using magnetic resonance imaging for monitoring the temperature of a tissue mass being heated in a focal zone encompassing at least a portion of the tissue mass, the focal zone being generally elongate and symmetrical about a focal axis, the method comprising:

acquiring a first plurality of images of the tissue mass in a first image plane aligned substantially perpendicular to the focal axis;

defining a cross-section of the focal zone in the first image plane from the first plurality of images;

acquiring a second plurality of images of the tissue mass in a second image plane aligned substantially parallel to the focal axis, the second image plane bisecting the first image plane at approximately a midpoint of the defined focal zone cross-section; and deriving a three-dimensional thermal evolution of the tissue mass in the focal zone based on the first and second pluralities of images.

8. The method of claim 7, wherein the heating energy is applied for a defined heating period, and wherein an image of the second plurality of images is acquired proximate an end of the heating period.

9. The method of claim 7, wherein the thermal evolution is derived by defining a cross-section of the focal zone in the second image plane from the second plurality of images, the cross-section of the focal zone in the second image plane being generally longitudinal and having a length, and extrapolating the cross-section of the focal zone in the first image plane along the length of the cross-section of the focal zone in the second image plane.

10. The method of claim 7, further comprising verifying that the temperature of the tissue mass in the focal zone exceeded a threshold temperature or thermal dose based on the derived thermal evolution.

11. The method of claim 7, further comprising acquiring one or more additional images of the tissue mass in the focal zone in a third image plane aligned substantially perpendicular to the focal axis while acquiring the images of the second plurality of images, defining a cross-section of the focal zone in the third image plane, and verifying that the second imaging plane bisects the third image plane at approximately a midpoint of the defined focal zone cross-section in the third image plane.

12. A system for monitoring changes in temperature of a tissue mass being heated by energy converging in a focal zone encompassing at least a portion of the tissue mass, the focal zone generally elongate and symmetrical about a focal axis, the system configured to:

acquire a first plurality of magnetic resonance images of the tissue mass in a first image plane aligned substantially perpendicular to the focal axis;

define a cross-section of the focal zone in the first image plane from the first plurality of images; and acquire a second plurality of images of the tissue mass in a second image plane aligned substantially parallel to the focal axis, the second image plane bisecting the first image plane at approximately a midpoint of the defined focal zone cross-section.

13. The system of claim 12, wherein the heating energy is applied for a defined heating period, and wherein an image of the second plurality of images is acquired proximate an end of the heating period.

14. The system of claim 12, further configured to derive a three-dimensional thermal evolution of the tissue mass in the focal zone based on the first and second pluralities of images.

15. The system of claim 14, wherein the thermal evolution is derived by defining a cross-section of the focal zone in the second image plane from the second plurality of images, the cross-section of the focal zone in the second image plane having a length, extrapolating the cross-section of the focal zone in the first image plane along the length of the cross-section of the focal zone in the second image plane, and determining differences in a characteristic of the tissue mass in the focal zone measured in successive images of the second plurality of images, the differences in the measured characteristic corresponding at least in part to changes in temperature of the tissue mass between respective images.

16. The system of claim 12, further configured to verify that the temperature of the tissue mass in the focal zone exceeded a threshold temperature or thermal dose based on the derived thermal evolution.

17. The system of claim 15, further configured to acquire one or more additional images of the tissue mass in the focal zone in a third image plane aligned substantially perpendicular to the focal axis between acquiring images of the second plurality of images, define a cross-section of the focal zone in the third image plane, and verify that the second imaging plane bisects the third image plane at approximately a midpoint of the defined focal zone cross-section in the third image plane.

18. A system for monitoring changes in temperature of a tissue mass being heated by energy converging in a focal zone encompassing at least a portion of the tissue mass, the focal zone generally elongate and symmetrical about a focal axis, the system configured to:

acquire a first plurality of magnetic resonance images of the tissue mass in a first image plane aligned substantially perpendicular to the focal axis, the first plurality of images including a baseline image taken prior to the application of ultrasound energy to the tissue mass;

define a cross-section of the focal zone in the first image plane from the first plurality of images; and acquire a second plurality of images of the tissue mass in a second image plane aligned substantially parallel to the focal axis, the second image plane bisecting the first image plane at approximately a midpoint of the defined focal zone cross-section, wherein the system derives a three-dimensional thermal evolution of the tissue mass in the focal zone based on the first and second pluralities of images.

19. The system of claim 18, wherein the energy is applied for a defined heating period, and wherein an image of the second plurality of images is acquired proximate an end of the heating period.

20. The system of claim 18, wherein the thermal evolution is derived by defining a cross-section of the focal zone in the second image plane from the second plurality of images, the cross-section of the focal zone in the second image plane having a length, extrapolating the cross-section of the focal zone in the first image plane along the length of the cross-section of the focal zone in the second image plane, and determining differences in a characteristic of the tissue mass in the focal zone measured in successive images of the second plurality of images, the differences in the measured characteristic corresponding at least in part to changes in temperature of the tissue mass between respective images.

21. The system of claim 18, further configured to verify that the temperature of the tissue mass in the focal zone exceeded a threshold temperature or thermal dose based on the thermal evolution.

22. The system of claim 18, further configured to acquire one or more additional images of the tissue mass in the focal zone in a third image plane aligned substantially perpendicular to the focal axis between acquiring images of the second plurality of images, define a cross-section of the focal zone in the third image plane, and verify that the second imaging plane bisects the third image plane at approximately a midpoint of the defined focal zone cross-section in the third image plane.

* * * * *